US010314851B2

(12) United States Patent
Thilly et al.

(10) Patent No.: US 10,314,851 B2
(45) Date of Patent: Jun. 11, 2019

(54) METAKARYOCIDAL TREATMENTS

(71) Applicant: Massachusetts Institute of Technology, Cambridge, MA (US)

(72) Inventors: William G. Thilly, Winchester, MA (US); Elena V. Gostjeva, Winchester, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/126,369

(22) PCT Filed: Mar. 17, 2015

(86) PCT No.: PCT/US2015/020988
§ 371 (c)(1),
(2) Date: Sep. 15, 2016

(87) PCT Pub. No.: WO2015/142865
PCT Pub. Date: Sep. 24, 2015

(65) Prior Publication Data
US 2017/0079992 A1 Mar. 23, 2017

Related U.S. Application Data

(60) Provisional application No. 61/954,426, filed on Mar. 17, 2014.

(51) Int. Cl.
*A61K 31/65* (2006.01)
*A61K 31/155* (2006.01)
*A61K 31/167* (2006.01)
*A61K 31/277* (2006.01)
*A61K 31/401* (2006.01)
*A61K 31/415* (2006.01)

(52) U.S. Cl.
CPC ............ *A61K 31/65* (2013.01); *A61K 31/155* (2013.01); *A61K 31/167* (2013.01); *A61K 31/277* (2013.01); *A61K 31/401* (2013.01); *A61K 31/415* (2013.01)

(58) Field of Classification Search
None
See application file for complete search history.

(56) References Cited

U.S. PATENT DOCUMENTS

| 7,427,502 | B2 | 9/2008 | Gostjeva et al. |
| 7,977,092 | B2 | 7/2011 | Gostjeva et al. |
| 8,465,943 | B2 | 6/2013 | Gostjeva et al. |
| 8,940,500 | B2 | 1/2015 | Gostjeva et al. |
| 2006/0063144 | A1 | 3/2006 | Gostjeva et al. |
| 2009/0081720 | A1 | 3/2009 | Gostjeva et al. |
| 2009/0098562 | A1 | 4/2009 | Gostjeva et al. |
| 2010/0075366 | A1 | 3/2010 | Gostjeva et al. |
| 2013/0203048 | A1 | 8/2013 | Gostjeva et al. |
| 2014/0369934 | A1 | 12/2014 | Thilly et al. |
| 2016/0011175 | A1 | 1/2016 | Gostjeva et al. |
| 2016/0024577 | A1 | 1/2016 | Gostjeva et al. |
| 2017/0081698 | A1 | 3/2017 | Thilly et al. |

FOREIGN PATENT DOCUMENTS

| WO | 2008/156629 A2 | 12/2008 |
| WO | 2010/036322 A1 | 4/2010 |
| WO | 2012/061073 A1 | 5/2012 |
| WO | 2012/167011 A1 | 12/2012 |

OTHER PUBLICATIONS

Young, et al. (2006) "Phase II clinical trial results involving treatment with low-dose daily oral cyclophosphamide, weekly vinblastine, and rofecoxib in patients with advanced solid tumors", Clinical Cancer Research, 12(10): 3092-98.*
Wysocki, et al. (2006) "Captopril, an Angiotensin-Converting Enzyme Inhibitor, Promotes Growth of Immunogenic Tumors in Mice", Clinical Cancer Research, 12(13): 4095-102.*
Son, et al. (2009) "Doxycycline Induces Apoptosis in PANC-1 Pancreatic Cancer Cells", Anticancer Research, 29(10): 3995-4004.*
Author uknown (Referred to as "Harvard Health Letter") (Apr. 2009) "The Whipple Procedure", Harvard Health Publishing, Harvard Medical School, https://www.health.harvard.edu/newsletter_article/The_Whipple_procedure, Harvard University, Boston MA, 4 pages long.*
International Preliminary Report on Patentability, dated Sep. 29, 2016, from International Application No. PCT/US2015/020933, filed on Mar. 17, 2015. Eight pages.
International Preliminary Report on Patentability, dated Sep. 29, 2016, from International Application No. PCT/US2015/020988, filed on Mar. 17, 2015. Sixteen pages.
Deng et al., "Celecoxib Downregulates CD133 Expression Through Inhibition of the Wnt Signaling Pathway in Colon Cancer Cells," Cancer Investigation, 31: 97-102 (2013).
Gostjeva et al., "Bell-shaped nuclei dividing by symmetrical and asymmetrical nuclear fission have qualities of stem cells in human colonic embryogenis and carcinogensesis," Cancer Genetics and Cytogenetics, 164: 16-24 (2006).
Gostjeva et al., "Metakaryotic stem cell lineages in organogenesis of humans and other metazoans," Organogenesis, 5(4): 191-200 (2009).
Gostjeva et al., "Nuclear Morphotypes in Human Embryogenesis and Carcinogenesis: Bell-Shaped Nuclei Show Stem-Like Properties in Vivo," Environmental and Molecular Mutagenesis, 47(6): 405 (2006) (Abstract Only).
Gostjeva et al., "Stem Cell Stages and the Originos of Colon Cancer: A Multidisciplinary Perspective," Stem Cell Reviews, 1: 243-252 (2005).

(Continued)

*Primary Examiner* — Robert M Kelly
(74) *Attorney, Agent, or Firm* — HoustonHogle LLP; Doreen M. Hogle

(57) ABSTRACT

The invention provides, inter alia, methods of treating a disorder characterized by excessive metakaryotic stem cell growth by a combination metakaryocidal therapy. Also encompassed by the present invention are preventative methods comprising the administration of a metakaryocidal or metakayrostatic therapeutic agent.

10 Claims, 4 Drawing Sheets

(56) References Cited

OTHER PUBLICATIONS

Herrero-Jimenez et al., "Mutation, cell kinetics, and subpopulations at risk for colon cancer in the United States," Mutat. Res., 400: 553-578 (1998).

Herrero-Jimenez et al., "Population risk and physiological rate parameters for colon cancer. The union of an explicit model for carcinogenesis with the public health records of the United States," Mutat. Res., 447: 73-116 (2000).

Hirsch et al., "Metformin Selectively Targets Cancer Stem Cells, and Acts Together with Chemotherapy to Block Tumor Growth and Prolong Remission," Cancer Res, 69: 7507-7511 (2009).

Hong et al., "CD44-Positive Cells are Responsible for Gemcitabine Resistance in Pancreatic Cancer Cells," Int. J. Cancer, 125: 2323-2331 (2009).

Iliopoulos et al., Metformin Decreases the Dose of Chemotherapy for Prolonging Tumor Remission in Mouse Xenografts Involving Multiple Cancer Cell Types, Cancer Res, 71: 3196-3201 (2011).

Kast et al., A Conceptually New Treatment Approach for Relapsed Glioblastoma: Coordinated Undermining of Survival Paths with Nine Repurposed Drugs (CUSP9) by the International Initiative for Accelerated Improvement of Glioblastoma Care, Oncotarget, 4: 4 (2013).

Lee et al., "Angiotensin-converting Enzyme Inhibitors Enhance the Effect of Cyclooxygenase Inhibitors on Breast Cancer: A Nationwide Case-Control Study," J. Hypertens, 30(12): 2432-2439 (2012).

Nangia-Makker et al., "Metformin: A Potential Therapeutic Agent for Recurrent Colon Cancer," PLoS ONE, 9(1) e84369 (2014).

Rattan et al., "Metformin: An Emerging New Therapeutic Option for Targeting Cancer Stem Cells and Metastasis," Journal of Oncology, Article ID 928127; 1-12 (2012).

Sagar et al., "Lowering the Apoptotic Threshold in Colorectal Cancer Cells by Targeting Mitochondria," Cancer Cell International, 10(31) 1-8 (2010).

Takehara et al., "Acetaminophen-Induced Differentiation of Human Breast Cancer Stem Cells and Inhibition of Tumor Xenograft Growth in Mice," Biochemical Pharmacology, 81: 1124-1135 (2011).

Thilly et al., "Metakaryotic stem cell nuclei use pangenomic dsRNA/DNA intermediates in genome replication and segregation," Organogenesis, 10(1) (2014). Sixteen pages.

Uslu et al., "Hepatic Progenitor Cell Inhibition during Embryonic Period with High Dose Verapamil; Liable Joint to the Cancer Therapy," Bratislava Medical Journal, 114(7): 369-375 (2013).

Venkatesan et al., "AEE788 Potentiates Celecoxib-Induced Growth Inhibition and Apoptosis in Human Colon Cancer Cells," Life Sciences, 91: 789-799 (2012).

Zheng et al., "Effects of Atorvastatin, Celecoxib and Tipifarnib Alone or in Combination on the Growth of Pancreatic Cancer in Panc-1 Cells Cultured in vitro or Panc-1 Tumors Grown in Immunodeficient Mice," Abstract of Presentation, AACR 101st Annual Meeting, American Association for Cancer Research: Philadelphia (2010).

International Search Report and Written Opinion of the International Searching Authority, dated Jun. 22, 2015, from International Application No. PCT/US2015/020933, filed on Mar. 17, 2015. Eleven pages.

International Search Report and Written Opinion of the International Searching Authority, dated Oct. 28, 2015, from International Application No. PCT/US2015/020988, filed on Mar. 17, 2015. Twenty-five pages.

\* cited by examiner

Effect of metformin concentration x duration of treatment in HT-29 cells.

| Week of treatment | Control | | | | | | |
|---|---|---|---|---|---|---|---|
| 1 week | ~375 colonies | ~381 colonies | ~370 colonies | ~370 colonies | ~330 colonies | ~330 colonies | ~300 colonies |
| 2 weeks | ~400 colonies | ~360 colonies | ~350 colonies | ~345 colonies | ~333 colonies | ~350 colonies | ~250 colonies |
| 2 weeks | ~390 colonies | ~375 colonies | ~345 colonies | ~340 colonies | ~342 colonies | ~350 colonies | ~250 colonies |
| 5 weeks | ~375 colonies | ~366 colonies | ~330 colonies | ~341 colonies | ~327 colonies | ~150 colonies | 0 colonies |

FIG. 2

METAKARYOCIDAL TREATMENTS

RELATED APPLICATION(S)

This application is a U.S. National Phase of International Application No. PCT/US2015/020988, filed on Mar. 17, 2015, which claims the benefit under 35 U.S.C. § 119(e) of U.S. Provisional Application No. 61/954,426, filed on Mar. 17, 2014. The entire teachings of the above application(s) are incorporated herein by reference.

BACKGROUND OF THE INVENTION

After the early embryonic stages of development and plants and animals, metakaryotic stem cells arise from metamorphoses of embryonic stem cells. They drive the growth and development of organs up to maturity and in animals have been found to persist in a quiescent state "on call" to serve as the stem cells of wound healing. However, disorders such as cancers, vascular diseases, post-surgical restenoses and scleroderma are driven by the abnormal growth and proliferation of this unique cell type known as metakaryotes or metakaryotic stem cells. Given the pervasiveness of these disorders, their immense social and financial costs to society, the dearth of effective treatment for these disorders, and the peculiar biology of metakaryotic stem cells (which, at least in part, is the reason for the ultimate ineffectiveness of existing treatments), a need exists for effective treatments for disorders characterized by excessive metakaryotic stem cell growth and, of greater long term public health importance, to prevent such disorders.

SUMMARY OF THE INVENTION

The present invention covers methods of treating and preventing disorders characterized by excessive metakaryotic stem cell growth in a mammalian subject in need thereof comprising providing a therapeutically effective metakaryocidal treatment, and in particular a combination metakaryocidal therapy, in which exposure of the subject to one or more separate metakaryocidal drugs is continuous and uninterrupted for a time/duration and at a dosage sufficient to achieve a blood concentration (i.e., therapeutic concentration) to effectively kill, or significantly inhibit the growth of metakaryotic stem cells thereby treating, or preventing, the disorder. The methods described herein can also include the administration of concurrent or sequential eukaryocidal treatment which effectively kills eukaryotic cells derived in part from differentiation of the metakaryotic cells growing in the pathogenic lesion in the subject.

In one embodiment, an effective metakaryocidal treatment method, as described herein, can comprise the administration of a single therapeutically effective amount of a metakaryocidal agent. Candidate metakaryocidal/metakaryostatic agents can be evaluated for their therapeutic efficacy using the methods described in International Application Number PCT/US15/20933, now US 2017/0081698 A1, the teachings of which are hereby incorporated herein in their entirety.

As described herein, a therapeutically effective amount of metakaryocidal agent is an amount sufficient so as to achieve plasma concentrations of the agent for an uninterrupted duration substantially similar to the in vitro metakaryocidal concentrations found to be metakaryocidal in HT-29 or CAPAN-1 cell cultures for uninterrupted durations sufficient to kill >99% of metakaryotic stem cells within the precursor lesion(s) of the disorder, e.g. an adenomatous polyp of the human colon, a precursor of lethal adenocarcinomas and metastases as described in the above-referenced application.

In another embodiment of the present invention, an effective combination metakaryocidal therapy comprises concurrent or sequential administration of two, three, four, five or more courses of effective metakaryocidal agents. Importantly, the administration of the metakaryocides (and eukaryocides if applicable) comprises administering two or more metakaryocidal agents so as to achieve plasma concentrations of the agents for an uninterrupted duration substantially similar to the in vitro metakaryocidal concentrations of the agents found to be metakaryocidal in HT-29 or CAPAN-1 cell cultures, as described above. That is, the effective course of metakaryocidal treatment for each single agent/drug, or combination of agents/drugs is of a sufficient dosage of, and uninterrupted duration of time sufficient to kill metakaryotes associated with excessive metakaryotic stem cell growth.

However, although the translation of effective treatment from a cell culture to a human subject or other animal subject will be based on the drug concentration effective in cell culture, but will not necessarily be of he duration of uninterrupted treatment effective in a cell culture. Those skilled in the art, and as described in International Application Number PCT/US15/20933, now U.S. Patent Application Publication No. US 2017/0081698 A1, will understand that metakaryotic stem cells may divide symmetrically and/or asymmetrically every day in cell culture but at much longer intervals in pathogenic lesions such as tumors or metastases, e.g. every twelve days in early human colonic adenocarcinomas. However, it is reasonable to believe that the duration of treatment effective in cell culture is translated to an effective treatment in mammals or humans when the duration of uninterrupted treatment in mammals is substantially equivalent to the number of symmetrical plus asymmetrical metakaryotic cell divisions found to be effective in cell culture. Thus, for example, a treatment with a single metakaryocide found effective for an uninterrupted duration of five days in a cell culture comprising sequential symmetric plus asymmetric divisions of metakaryotes in culture can reasonably require exposure of metakaryotes in a subject for a duration of up to weeks or months (e.g., about 60 or more days to achieve an exposure period of five intervals between symmetric plus asymmetric divisions of 12 days per interval) to be effective in a human colonic adenocarcinoma.

The methods of the present invention encompass an effective metakaryocidal therapy wherein the metakaryocidal drugs contemplated to be administered to the subject comprise an effective amount of any single, or combination of two or more agents such as acetaminophen, aspirin, captopril, celecoxib, daunorubicin, doxycycline, glyburide, metformin, verapamil or other NSAIDs, antibiotics or other agents identified as metakaryocidal to metakaryotic stem cells in culture or explants derived from lesions of mammalian/human disorders. In particular, based on observations of two weeks exposure of HT-29 cells in cell culture, the methods comprise administering metakaryocides at a concentration and for a time sufficient for an effective therapy wherein the amount of captopril achieves a plasma concentration of about 0.125 to about 0.5 µM (e.g., about 0.25 µM), the effective amount of celecoxib achieves a plasma concentration of about 12.5 to about 50 µM (e.g., about 25 µM), the effective amount of doxycycline achieves a plasma concentration of about 2.5 to about 10 µM (e.g., about 5 µM), the effective amount of metformin achieves a plasma concentration of about 100 to about 800 µM (e.g., about 200 µM), and the effective amount of verapamil achieves a plasma concentration of about 2 to about 8 μM (e.g., about 4.0 μM). The metakaryocidal treatments described herein as single or combination metakaryocidal therapy are each administered for a period of about 2, 3, 4, 5, 6, 7, 8, 9, 10, 11, 12, or 13 weeks. The combination therapy can further encompass a resting interval of 1, 2, 3 or more days, or 1 or 2 or more weeks or months between the administration of the metakaryocidal agents. Moreover, these drugs at concentrations indicated can be effective for the prevention (i.e., decreased likelihood) of diseases in which metakaryotes serve as the stem cells of precursor lesions when used singly over a sufficient uninterrupted period that kills at least 99% of the metakaryotic stem cells of the precursor lesion. Determination of effective "killing" of metakaryotic cells, or the identification of viable and non-viable metakaryotes, is described herein, and in International Application Number PCT/US15/20933, now U.S. Patent Application No. US 2017/0081698 A1.

In a particular embodiment of the present invention the mammalian subject is a human and the disorder characterized by excessive metakaryotic stem cell growth is cancer, for example, pancreatic cancer. Also encompassed by the present invention are disorders characterized by excessive metakaryotic stem cell growth such as atheroscleroses, venoscleroses, post-surgical restenoses, scleroderma or diabetes mellitus.

The present invention further encompasses kits comprising dosage forms of one, two or more metakaryocidal agents suitable for treating or preventing a disorder characterized by excessive metakaryotic stem cell growth in a mammalian subject in need comprising two, three, four, five or more metakaryocides in the application as a therapy, or when applied for disease prevention. Use of a metakaryocidal agent as described herein, for the preparation of medicament for treating a disorder characterized by excessive metakaryotic stem cell growth in a mammalian subject in need thereof by means of a combination metakaryocidal therapy is also encompassed by the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 2 is a table illustrating the effects of combinations of metformin concentrations and durations of treatment of HT-29 cells.

DETAILED DESCRIPTION OF THE INVENTION

A description of example embodiments of the invention follows.

The teachings of all patents, published applications and references cited herein are incorporated by reference in their entirety.

The invention is based, at least in part, on Applicants' discovery of a growing number of drugs already used for diverse medical purposes in the United States that have now been found capable of killing growing metakaryotic stem cells in cell lines derived from adenocarcinomas of the human colon (HT-29) and pancreas (CAPAN-1). Most of these drugs were metakaryocidal at concentrations in cell culture known to be well below plasma concentrations associated toxic side effects in humans. Some of the metakaryocidal drugs identified so far are effective in cell culture at concentrations in the blood plasma well tolerated by patients using these drugs treatment of other maladies, e.g. doxycycline when used as an antibiotic.

From these cell culture experiments, Applicants' previous discovery that human stem cells during lung and colon organogenesis have extraordinarily high mutation rates compared to eukaryotic non-stem cells (Sudo et al., 2008; Kini et al, 2013) and certain mathematical considerations. Applicants have devised a novel course of therapy and prevention comprising a single therapeutically effective drug (e.g., for prevention purposes) or a single, or a set of multi-drug treatment regimens to treat metakaryotic stem cell derived diseases (e.g. diseases associated with metakaryotic stem cells). These regimens are designed to kill all, or significantly inhibit the growth of, growing metakaryotic stem cells in mammalian cancers, and their metastases, and to furthermore capture and kill such residual non-dividing cancer stem cells existing at the initiation of treatment.

The stem cells of human organogenesis and wound healing are not eukaryotic but metakaryotic cells, a cell form previously recognized by Applicants. Applicants subsequently discovered that metakaryotic cells are also the stem cells of pathological processes including carcinogenesis, atherogenesis and post-surgical restenosis.

Figure 4A:
FIGS. 4A and B show surviving metakaryotic cells in a sample of a lung tumor taken from an adult patient after extended treatment with radio- and chemotherapy. Nuclei of eukaryotic cells are pyknotic but nuclei of metakaryotic are not pyknotic, illustrating that present standards of care using radio- and chemotherapies kill eukaryotic-non stem cells but not metakaryotic stem cells in treated tumors.
Figure 4B:
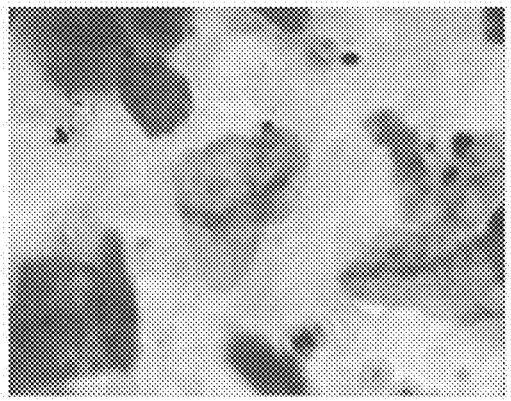

Metakaryotic cells differ from eukaryotic cells in many characteristics of cellular and molecular biology but, in particular, are relatively resistant to killing by agents that kill eukaryotic cells in growth phase such as x-rays, radiomimetic and anti-metabolic agents widely used to treat cancers. Such eukaryocidal agents kill eukaryotic cells in cancerous lesions such as adenocarcinomas in which, for example, they comprise the cells of the epithelial portion of the lesion. Present standards of practice for treatments of tumors and metastases include regimens of x-irradiation and chemotherapy with one or more drugs that kill actively dividing eukaryotic cells of the lesion. Treatments of this kind kills a large fraction of eukaryotic cells of the lesion recognized by x-ray or CT scan as shrinkage of the tumor mass in which microscopic examination reveals dead eukaryotic but not metakaryotic cells (FIG. 4). Applicants earlier discovered that the metakaryotic stem cells in cell cultures were not significantly affected by such commonly applied cancer treatments. After standard radio- and chemo-therapeutic treatments the metakaryotic stem cells rapidly regenerate the tumor (relapse) leading to death.

Applicants reasoned that agents that killed metakaryotic cells might be used in treating pathological lesions in which metakaryotic cells served as the stem cells that drove the growth of the lesions. They similarly reasoned that reduction of the metakaryotic stem cells of a preneoplastic lesion by metakaryocidal treatment could reduce the number of surviving metakaryotic stem cells so that the subsequent age-specific incidence of the disease could be reduced on the order of a hundred fold using treatment that would kill >99% survival of metakaryotic precancerous stem cells within the preneoplastic lesions of a subject's body).

Applicants next sought means to test nominated drugs (also referred to herein as candidate agents) using human cell cultures, particularly cell cultures derived from human tumors in which they discovered metakaryotic cells driving net growth and differentiation of such cultures by symmetric and asymmetric amitotic divisions. Two cell lines in particular HT-29 (derived from a human colonic adenocarcinoma) and Capan-1 (derived from a human pancreatic adenocarcinoma) were found to have these characteristics. With these lines they tested nominated drugs by observing (a.) evidence of disrupted or dead (pyknotic) metakaryotic cells and (b.) reduction of stem cell number evidenced by reduction of the fraction of treated cells that gave rise to immortal colonies that invariably contained metakaryotic stem cells, as described in International Application Number PCT/US15/20933, now U.S. Patent application No. US 2017/0081698 A1.

Applicants discovered that, unlike the effects of x-rays or drugs commonly used to treat cancers, nominated drugs did not kill metakaryotes in one, two or three days of exposure to concentrations representing the highest doses known to be tolerated by humans. Unexpectedly, sustained treatment for five consecutive days or longer was required to observe cytotoxic or immortal colony suppressing effects of these drugs at concentrations tolerated at plasma levels in humans. Applicants noted that some of the drugs that they found to be metakaryocidal in their assays had been tested in clinical trials using short exposure periods alone or in combination with eukaryocidal "chemotherapeutic" drugs and under the conditions of treatment had been reported to be ineffective.

Applicants noted that interruption in treatment with metakaryocidal drugs in cell cultures resulted in greatly reduced metakaryocidal effect. It was recognized that patient plasma concentrations would therefore need to be maintained at about metakaryocidal concentrations throughout the course of treatment in order to be effective in killing all cancer metakaryotic stem cells (also referred to herein as the "course of effective treatment") or nearly all (>99%) metakaryotic stem cells of precancerous lesions or early pre-atherosclerotic plaques (also referred to herein as course of effective preventive treatment). Monitoring of patients with regard to said metakaryocidal agent plasma concentrations would thus be desirable, more probably necessary, as variation among patients and induction of physiological responses leading to more rapid drug clearance would be anticipated with prolonged treatments.

Applicants measured the distribution of mutant colony number and sizes in adult human lungs and discovered the distribution indicated an unexpectedly high and constant mutation rate in the stem cells of human lung organogenesis, some hundreds to thousands of times higher than found by applicants and others in human eukaryotic cells (Sudo et al., 2008. Applicants ascribed these high mutation rates to the peculiar mode of genome replication they had discovered in metakaryotic cells (Thilly et al., 2014).

Applicants had previously studied mutations resulting in loss of drug binding capacity and drug sensitivity in human cells and found that the rate of such mutations was some one hundred times lower than the rates of mutations that inactivated a gene product (Leong et al., 1985).

Applicants then used their knowledge of mutation rates in human organogenesis to hypothesize that a tumor or tumor metastasis would contain many metakaryotic stem cells resistant to any one metakaryocidal drug that acted by, e.g., binding to and inactivating a target molecule in a metakaryotic cancer stem cell. They thus recognized the possibility that multiple metakaryocidal drugs acting, preferably independently, would probably be necessary to kill an effective number (e.g., all) metakaryotic cancer stem cells in a patient or >99% in a preneoplastic lesion or other asymptomatic precursor of a disease in which metakaryotic cells serve as the stem cells. Applicants considered the number of expected metakaryotic stem cells and the rates of mutations in human organogenic metakaryotic stem cells and determined that a combination of drugs, preferably, two, three or four metakaryocidal drugs would be effective to treat the majority of cancer patients, while five or more drugs might be required in a minority of patients.

Applicants had previously considered the period of time between stem cell divisions in adult humans Based on quantitative enumeration of dividing and dying eukaryotic cells in the normal colonic epithelium, colonic adenomas and early adenocarcinomas they estimated that the average time interval between stem cell divisions (symmetric plus asymmetric divisions) was ~128, ~40 and ~12 days respectively and indirectly estimated it might be on the order of 5-7 days in peritoneal metastases. Because Applicants were aware from cell culture studies that not all cells capable of continued growth are actively growing at any time they hypothesized that treatment with metakaryocidal drugs should continue a period greater than represented by the estimated average of about 12 days between metakaryotic divisions in early colorectal tumors.

Applicants have devised means to use cell populations derived from pathologic lesions comprising these diseases in quantitative assays that permit recognition of drugs that in sufficient concentration and duration of uninterrupted application are lethal to metakaryotic stem cells and their immediate precursors. (International Application Number PCT/US15/20933, now U.S. Patent Application No. US 2017/0081698 A1) They have discovered multiple drugs having these qualities and found that some of them are drugs that have been used in treating other human disorders in millions of people for many decades but that have not been applied so as to provide an uninterrupted period of application at an effective concentration that together are required for metakaryocidal activity and treatment of metakaryotic diseases.

Applicants' findings and hypotheses indicated that a series of treatments, e.g., five treatments, with metakaryocidal drugs, with each drug treatment maintained in the patient's blood (plasma or serum) at an effective metakaryocidal concentration for an uninterrupted duration of, for example, about 36 days would en toto expose the metakaryotic cancer stem cells of a patient to about 180 days of effective treatment. Such a regimen of treatment would reasonably be expected to kill all resident metakaryotic cancer stem cells and as a result offer the possibility of complete elimination of the subject's cancer. Applicants note that the first of four of five metakaryocidal treatments is expected to kill between 99 and 99.99% of all cycling metakaryotic stem cells of the lesion and that the second, third, fourth and any additional uninterrupted treatments with other metakaryocidal agents are used to achieve the necessary goal of killing all cycling metakaryotic stemcells of the lesion under treatment. Applicants note that the extended period required for multiple sequential treatments provides a necessary extended opportunity to kill metakaryotic stem cells of the lesion as many may have been quiescent at the beginning of metakaryocidal treatments. Applicants note that treatment of a lesion with metakaryocides and/or eukaryocides is expected to provoke a wound healing response among the metakaryotic stem cells of the lesion specifically provoking quiescent metakaryotic stem cells in the lesion to begin active cell divisions that render them sensitive to metakaryocidal drugs.

Although the period of a course of effective treatment would be of necessity continuous and uninterrupted for each metakaryocidal drug administered, there may be an interval of respite (e.g., a resting interval) between courses of effective treatment with each of the metakaryocidal drugs. The resting interval may be for a few days, to one to two weeks, or more up to about one to two months. For example, Drug A could be administered to the patient for a period of time and dosage sufficient to kill metakaryotes (e.g., for about 36 days) and prior to beginning treatment with Drug B, a period of one to two weeks could ensue without metakaryocidal treatment.

It is important to note that the treatments described herein also encompass treatment with a metakaryocidal agent to destroy most, but not all, of the metakaryotic stem cells of a slowly growing pre-lethal lesion such as a colonic adenomatous polyp. Such treatment can be accomplished by continuous treatment at an effective concentration for a duration of as long as one year to permit action of the drug through successive intervals of metakaryotic stem cell divisions, symmetric and asymmetric. For example, nine successive intervals between the asymmetric divisions of metakaryotic stem cells of such slowly growing lesions as human colonic adenomas is roughly equivalent to 360 days or one year. Such treatment is expected to greatly reduce the subsequent appearance of tumors throughout the lifetime of the individual undergoing such preventive continuous exposure to a metakaryocide at an effective plasma concentration.

Disorders to be Treated

As described above, the disorders to be treated encompass any disorder characterized, or associated with, or derived from, excessive metakaryotic cell growth. Specifically encompassed by the present invention is cancer. A disorder/disease "characterized by excessive metakaryotic stem cell growth" includes both monoclonal (e.g., cancer, atherosclerosis, venosclerosis) and polyclonal (e.g., restenosis or scleroderma) disorders where metakaryotic cells undergo excessive growth or division-including either asymmetrical or symmetrical divisions. In particular embodiments, a monoclonal disorder characterized by excessive metakaryotic stem cell growth is cancer, including carcinomas, sarcomas, hematological cancers (lymphoma and leukemia), germ cell tumors, and blastomas. In more particular embodiments the cancer is selected from bladder, brain, breast, colon, rectal, endometrial, leukemia, lung, hepatic (e.g., HCC), kidney, melanoma, non-Hodgkin lymphoma, prostate, pancreatic, stomach, and thyroid cancer and combinations thereof. The cancer may be either localized (non-metastatic) or metastatic. Additional states that may be related to cancer and that can be treated by the methods provided by the invention include precancerous lesions and neoplasias. Additional disorders characterized by excessive metakaryotic stem cell growth include type II diabetes (which Applicants perceive as a metakaryotic disease based on the identity of its age-specific mortality to the function observed for many common cancers such as colorectal, pancreatic, esophageal and prostate cancers and the finding by others that at least one form of diabetes is caused by a very small, specific form of pituitary neoplastic lesion) endometriosis, polycystic diseases, and benign malignancies.

In still other embodiments, the disorder characterized by excessive metakaryotic stem cell growth is polyclonal, including disorders such as restenosis, also known as "galloping atherosclerosis" or the ultimately lethal disease scleroderma. In the case of vascular restenoses applicants have specifically observed the creation of smooth muscle cells that in overabundance characterize this type of lesion arising by asymmetric amitoses from metakaryotic cells. In the case of scleroderma, applicants have specifically observed metakaryotic stem cells undergoing amitoses and creating the many non-stem cells of these lesions by asymmetric amitoses.

Metakaryotes

"Metakaryote, "metakaryotic stem cell," and the like refer to cells characterized by, inter alia, a bell-shaped nucleus, where the cell divides by amitosis-either symmetrical or asymmetrical. Metakaryotes have been observed in both animal (insect, mammalian as well as human), and plant cells. Metakaryotes also exhibit a double-stranded hybrid RNA/DNA intermediate genome during division. See, e.g., International Application Publication No. WO 2012/167011, incorporated by reference in its entirety. Metakaryotes can be in the form of either an individual cell with a single nucleus or multinucleate syncytial structures. Metakaryotes are first observed early in human organogenesis in weeks 4-7 arising from pre-metakaryotic cells that do not have bell shaped nuclei but which develop them before giving rise to two bell shaped nuclei by a specialized form of "kissing bell" amitoses (Gostjeva et al. 2009). Herein reference to killing of metakaryotic cells is meant to include such pre-metakaryotic cells as reasonably expected to occur that, if surviving treatment can give rise to new metakaryotes and support regrowth of the lesion or lesions requiring treatment. Cell culture studies demonstrate that both metakaryotic cells and hypothetical pre-metakaryotic cells, are effectively killed by the metakaryocidal drug treatment as shown for metformin in FIG. 3. The basis for this interpretation is that after treatment with the various metakaryocides cited, replating of treated cultures discovers no cells capable of further division as would be expected of surviving metakaryotic stem cells or hypothetical precursor cells.

The skilled artisan will be able to readily identify metakaryotic stem cells when practicing the methods provided by the invention. For example, the methods of identification, screening, diagnosis, prognosis and treatment provided herein can comprise the step of detecting metakaryotic stem cells from a tissue sample or in cultured cells by detecting an intermediate dsRNA/DNA duplex genome. Cultured cells or cells from within a tissue samples being visualized by the methods of the invention are prepared in a way that substantially preserves the integrity of nuclear structures in nuclei having maximum diameters up to about 10, 20, 30, 40, 50, 60, or 70 microns- and in more particular embodiments up to about 50 microns. Methods for preparing cells are also described in U.S. Pat. No. 7,427,502, the teachings of which are incorporated by reference in their entirety. In certain embodiments, the preparation substantially preserves the integrity of nuclear structures in metakaryotic nuclei of about 10-15 microns. For example, in some embodiments a tissue sample may be analyzed as a preparation of at least about 20, 30, 40, 50, 60, 70, 80, 90, 100, 150, 200, 250, 300, 350, 400, 450, 500, 750, 1000, 1250, 1500 or more microns in thickness. In certain embodiments, a tissue sample is macerated by, for example, incubation in about 45% (e.g., about 25, 30, 35, 40, 42, 45, 47, 50, 55, 60 or 65%) acetic acid in preparation for analysis. Alternately, the sample may be macerated by collagenase or other suitable protease (Gostjeva et al., 2009).

In some embodiments, to further facilitate detection of metakaryotes, cultured cells or tissue samples can be stained. In particular embodiments, the staining can comprise staining with, for example, a Schiffs base reagent, Feulgen reagent, or fuchsin. In more particular embodiments, the tissue sample may be further stained with a second stain. In still more particular embodiments, the second stain may be Giemsa stain.

In certain embodiments, metakaryotic stem cells can be detected by the fluorescence of their cytoplasm, following treatment with a non-fluorescent stain, such as Schiffs reagent. See, e.g., U.S. Patent Application Publication No. 2010/0075366 A1, including Example 5, FIGS. 20-27, and their descriptions, all of which are incorporated by reference. Metakaryotes involved in wound healing disorders, which generally do not exhibit Feulgen reagent-induced fluorescence in their balloon-shaped cytoplasmic structures, are described in International Application Publication No. WO 2012/061073, incorporated by reference in its entirety.

Treatment Modalities

A "combination metakaryocidal therapy" is a regimen of two or more (e.g. 2, 3, 4, 5, 6, or more) "metakaryocidal treatments"—i.e. chemical agents (such as a small molecule or biologic; "metakaryocidal agents") or environmental conditions (i.e. changes in temperature, pH, pressure, pO2, and combinations thereof; "metakaryocidal conditions") or a combination of chemical agent(s) and environmental condition(s)—that inhibit the growth or proliferation of cycling (i.e., non-dormant) metakaryotes and encompasses agents that reduce the number of metakaryotes (e.g., by killing the metakaryotes) or blocking an increase in the number of these cells—i.e., agents or treatments termed "metakaryostatic." Treatments can also include irradiation such as x-rays. Metakaryocidal treatments preferentially inhibit the growth or proliferation of cycling metakaryotes over cycling eukaryotes (e.g., by 50, 60, 70, 80, 90, 95%, or 2, 3, 4, 5, 6, 7, 8, 9, 10, 20, 30, 40, 50, 60, 70, 80, 90, 100, 200, 300, 400, 500, 600, 700, 800, 900, 1000-fold, or more). In certain embodiments, the regimen comprises concurrent metakaryocidal treatments. In other embodiments, the regimen comprises sequential metakaryocidal treatments. In still other embodiments, the regimen comprises both concurrent and sequential metakaryocidal treatments—e.g., a regimen comprising three metakaryocidal treatments, A, B, and C, may, in certain embodiments, entail concurrent treatment with two agents (e.g., A and B, A and C, or B and C) preceded or followed by treatment with the third agent (i.e., C, B, or A in the foregoing examples).

An "uninterrupted therapeutically effective combination metakaryocidal therapy" is a combination metakaryocidal therapy where each and all of the metakaryocidal drug treatments of the combination are maintained within an "effective range of metakaryocidal activity"—i.e., at or above the minimally effective (i.e., metakaryocidal) dose of a metakaryocidal agent and at or below the maximum tolerable dose of the metakaryocidal agent-over the entire course of effective therapy period; e.g., in some embodiments, for the entire approximately ~7 week period for each metakaryocidal treatment and over the entire combination of two or more (e.g., 4-6) treatments in the combination metakaryocidal therapy. This teaching specifically addresses the finding that under exposure to a particular metakaryocidal drug interruption of treatment greatly diminishes or even eliminates the effectiveness of treatment with that drug. However, a resting period between separate treatments with separate metakaryocidal drugs may in some cases be medically desirable, e.g., wherein surgery becomes necessary or when extended periods of combined metakaryocidal treatment induce presently unexpected side effects in normal tissues. Limits on such periods between metakaryocidal treatments are bounded by the expectation that overly extended periods would permit regrowth of metakaryotic cells and their precursors not killed by prior treatment.

Metakaryocidal agents include certain NSAIDs (non-steroidal anti-inflammatory agents) and other analgesics, including agents that inhibit both Cox-1 and Cox2 (such as acetaminophen or aspirin), or Cox-2 specific inhibitors (e.g., celecoxib); metformins; tetracyclines (e.g., doxycycline); ACE (angiotensin-converting enzyme) inhibitors (such as captopril); prostacyclin (PGI2) analogs (such as treprostinil, also known as REMODULIN®); sulfonylureas, phenylalkylamines (such as verapamil) and salinomycin.

A "subject" (i.e., to be treated by the methods provided by the invention) refers to a mammal, including primates (e.g., humans or monkeys), cows, sheep, goats, horses, dogs, cats, rabbits, guinea pigs, rats, mice or other bovine, ovine, equine, canine, feline, rodent or murine species. Examples of suitable subjects include, but are not limited to, human patients. In particular embodiments, the subject to be treated by the methods provided by the invention is human and can be male or female and may be used in treatments of adult humans (early adult, middle-age, or geriatric, e.g., at least or about 1, 2, 3, 4, 5, 6, 7, 8, 9, 10, 15, 18, 20, 21, 25, 30, 35, 40, 45, 50, 55, 60, 65, 70, 75, 80, 85, 90, 95, 100, 105 years old, or more) and other animals. However, as metakaryotes are also the stem cells of normal growth and development and wound healing of humans and other animals (Gostjeva et al., 2009) use in humans or other animals that have not reached maturity cannot be recommended: e.g., prenatal, neonatal, infant, toddler, juvenile patients. In like fashion, treatment of pregnant women with metakaryocides is expected to endanger the fetus for any metakaryocidal agent that reaches the fetus. An apparent important exception is the metakaryocidal drug metformin that does not cross the placental barrier and has been widely used to treat polycystic disease in pregnant women. Similarly, metakaryotic drugs should not be used for a period immediately before and after surgery, a caveat generally recognized in patients using drugs such as metformin now recognized by Applicants as metakaryocidal but without the understanding that the drug kills or retards the growth of metakaryotic stem cells essential for wound healing. Similarly, it is apprehended that in the use of sequential treatments with combinations of metakaryocides certain unknown roles of metakaryotes in maintaining adult tissue structures may become apparent such that as in the case of pre-surgical care, a period of time, e.g., two weeks between treatments with separate metakaryotic drugs may be preferred.

As used herein, the terms "treat," "treating," or "treatment," mean to counteract or prevent a medical condition (e.g., cancer, atherosclerosis, restenosis) to the extent that the medical condition is improved according to a clinically-acceptable standard.

The terms "prevent," "preventing," or "prevention," as used herein, mean reducing the probability/likelihood, progression, onset, risk or severity of a disorder-including, for example, cancer, atherosclerosis, or restenosis.

As used herein, a "therapeutically effective amount" is an amount sufficient to achieve the desired therapeutic or prophylactic effect under the conditions of administration, such as an amount sufficient to inhibit (e.g., reduce, prevent), e.g., a condition characterized by excessive metakaryotic stem cell growth. The effectiveness of a therapy can be determined by one skilled in the art using standard measures and routine methods.

In certain embodiments of the methods provided by the invention, the combination metakaryocidal therapy comprises administering one or more metakaryocidal agents so as to achieve plasma concentrations, in the subject being treated, of the agents "substantially similar" (i.e., within about 4-fold, 2-fold, or 1-fold but not lower than the effective in vitro metakaryocidal concentrations of the agents in cells in culture, such as in HT-29 or CAPAN-1 cells. "Metakaryocidal concentrations" of an agent are those that achieve at least a 99, 99.9, 99.99%, or more, reduction in the number of metakaryotes, preferentially over eukaryotes, in an HT-29 or CAPAN-1 culture (e.g., in some cases resulting in about 10-4 survival of metakaryotes), within about 10 interdivision periods, e.g., within about 1, 2, 3, 4, 5, 6, 7, 8, 9, or 10 weeks of "substantially constant" patient plasma levels—i.e., maintaining a concentration of the agent in the effective concentration range in patient's plasma. In more particular embodiments, the metakaryocidal dose in HT-29 or CAPAN-1 cells is determined by an assay as illustrated by the Exemplification.

In certain embodiments, the metakaryocidal therapy comprises administering an effective amount of one or more of captopril, celecoxib, doxycycline, metformin, verapamil, or acetaminophen, i.e., at least 1, 2, 3, 4, 5, or all 6 of these agents. Additional agents are being discovered by applicants through continued trials of different agents such that many more drugs are expected to be found to be metakaryocidal in concentration ranges well tolerated as concentrations in plasma. In more particular embodiments, the effective amount of captopril achieves a plasma concentration of about 0.25 µM (about, e.g., 0.025, 0.06, 0.09, 0.125, 0.19, 0.25, 0.31, 0.37, 0.43, 0.50, 0.56, 0.62, 0.68, 0.75, 1.0 or 2.5 µM; e.g., about 0.125-0.50 µM); the effective amount of celecoxib achieves a plasma concentration of about 25.0 µM (about, e.g., 2.5, 6.0, 9.0, 12.5, 19.0, 25.0, 31.0, 37.0, 43.0, 50.0, 56.0, 62.0, 68.0, 75.0, or 250 µM; e.g., about 12.5-50.0 µM), the effective amount of doxycycline achieves a plasma concentration of about 5.0 µM (about, e.g., 0.5, 1.25, 1.85, 2.5, 3.75, 5.0, 6.25, 7.5, 8.75, 10.0, 15.0, 20.0, or 50 µM; e.g., about 2.5-10.0 µM) the effective amount of metformin achieves a plasma concentration of about 400.0 µM (about, e.g., 40, 100, 150, 200, 300, 400, 500, 600, 700, 800, 1200, 1600, 4000 µM; e.g., about 200-800 µM), and the effective amount of verapamil achieves a plasma concentration of about 4.0 µM (about, e.g., 0.4, 1.0, 2.0, 3.0, 4.0, 6.0, 8.0, 12.0, 16.0, 40.0 µM; e.g., 2.0-8.0 µM). In still more particular embodiments 4-6 (e.g., 5) of these agents are administered sequentially (e.g., one-at-a-time) for about 4-6 (e.g., 5) weeks each over a total period of about 16-36 weeks (for example, about 25 weeks). By monitoring plasma levels of the metakaryocidal agents (or one or more metabolites thereof), a caregiver can maintain a therapeutically effective dosage of the agent, accounting for the subject's metabolism by adjusting the administered dose of the agent. In certain embodiments, the plasma concentration of the metakaryocidal agent is kept substantially constant, as defined above. The skilled artisan will appreciate that the target plasma concentrations of metakaryocidal agents and the target exposure period may be adjusted so as to achieve a similar time-dosage, e.g., by maintaining a lower plasma concentration of the agent for a longer period of time or, conversely, a higher plasma concentration for a shorter period of time. In particular embodiments, the target plasma concentration is less than ~25% of the maximum tolerated level for humans or other treated animals. Applicants recognize that distribution and therefore the effectiveness of metakaryocides to the metakaryotic stem cells to the lesions targeted for treatment of a subject is a function of processes of internal distribution, metabolism and clearance in the body and treated lesions that are not yet understood. The future study of pharmacokinetic and pharmacodynamic parameters that govern the levels of metakaryocidal drugs to their target metakaryotic stem cells are expected to add useful understanding regarding the use of metakaryocidal agent therapies in treatment and prevention of diseases in which metakaryotic stem cells are the driving force of lesion growth and differentiation.

The therapeutically effective plasma concentrations of the metakaryocidal agents are maintained via accepted means, such as periodic oral, intravenous, mucosal (e.g., rectally, nasally, or by inhalation) or transdermal (including IP) administration. For example, in certain embodiments, the metakaryocidal agents are administered orally and, in more particular embodiments, are administered orally approximately every, e.g., about 2, 3, 4, 5, 6, 7, 8, 9, 10, 12, 18, or 24 hours, or about 1, 2, 3, 4, 5, 6, 7 days, depending on, inter alia, the serum half-life for the subject and available dosage forms of the agent. In other embodiments, the agent is administered by a pump (optionally including a sensor to monitor plasma levels of the agent, a metabolite of the agent, or another correlate for the concentration of the agent) or a delayed release modality. In a preferred embodiment continuous infusion of metakaryocidal drugs are used with portable infusion pumps equipped with means to recognize, promptly respond to and record an infusion failure so as to ensure uninterrupted drug delivery.

In the methods provided by the invention, the metakaryocidal treatments of the combination metakaryocidal therapy are each administered for a period corresponding to about 2, 3, 4, 5, 6, 7, 8, 9, or 10 metakaryote doubling times (e.g., about 4-6 doubling times) for the particular tumor in the subject, e.g. about 2, 3, 4, 5, 6, 7, 8, 9, 10, 11, 12, or 13 weeks, e.g., about 3-7 weeks, e.g., about 5 weeks. In some embodiments, the treatments are each administered for this period and, as previously noted, the treatments can for some drug combinations be administered concurrently or for all series of drug treatments sequentially.

Effective dosages of metakaryocidal agents can also be further approximated by using effective dosages achieved in one animal and converting the dose for use in another animal, including humans, using conversion factors known in the art. See, e.g., Reagan-Shaw et al., *FASEB J.* 22:659-61 (2008); Schein et al., *Clin. Pharmacol. Ther.* 11: 3-40 (1970); and Freireich et al., *Cancer Chemother. Reports* 50(4):219 244 (1966). For example, human equivalent dosing (HED) in mg/kg based on animal dosing may be given by the following equation: HED (mg/kg)=animal dose (mg/kg)×($K_m^{animal}/K_m^{human}$), where Km=weight/surface area (kg/$.^{m2}$). Exemplary conversion factors based on the above equation are shown in the following table.

| To: | From: | | | | |
|---|---|---|---|---|---|
| | Mouse (20 g) | Rat (150 g) | Monkey (3.5 kg) | Dog (8 kg) | Human (60 kg) |
| Mouse | 1 | 0.5 | 0.25 | 0.17 | 0.08 |
| Rat | 2 | 1 | 0.5 | 0.25 | 0.14 |
| Monkey | 4 | 2 | 1 | 0.6 | 0.33 |
| Dog | 6 | 4 | 1.7 | 1 | 0.5 |
| Human | 12 | 7 | 3 | 2 | 1 |

In certain embodiments, the subject being treated by the methods provided by the invention, e.g., where the condition characterized by excessive metakaryotic stem cell growth is cancer, is also being treated, either concurrently or sequentially with one or more eukaryocidal treatments. "Eukaryocidal treatment" means conventional cancer treatments that kill or inhibit the growth of non-metakaryotic cancer cells. Exemplary eukaryocidal treatments include chemotherapy, radiation therapy, surgery, et cetera, such as treatment with gemcitabine (see, e.g., PubChem 60750, 60749, 11599950, 6420157, 44558863, 9828310), 5-fluorouracil ("5-FU", and related compounds; see, e.g., PubChem 3385, 25244711, 8642), methotrexate (see, e.g., PubChem 126941, 4112, 72440, 165528, 10713), a cis-platinum, or certain monoclonal antibodies In more particular embodiments, the treatment comprises surgery, such as a Whipple procedure and/or hepatic artery embolization for a subject with pancreatic cancer. In other embodiments, the eukaryocidal treatment comprises a gemcitabine treatment, such as a gemcitabine combination therapy (e.g., in combination with one or more of erlotinib (see, e.g., PubChem 176870, 176871, 18924996, 11599950); oxaliplatin (see, e.g., PubChem 5310940, 77994, 9887054); or 5-FU).

Agents (either metakaryocidal or eukaryocidal) for use in the methods provided by the invention can be delivered by any suitable route and in any suitable form. The pharmaceutical preparations disclosed herein are prepared in accordance with standard procedures and are administered at dosages that are selected to reduce, prevent, or eliminate, or to slow or halt the progression of, the condition being treated (see, e.g., Remington's Pharmaceutical Sciences, Mack Publishing Company, Easton, Pa., and Goodman and Gilman's The Pharmaceutical Basis of Therapeutics, McGraw-Hill, New York, N.Y., the contents of which are incorporated herein by reference, for a general description of the methods for administering various agents for human therapy). The compositions of a compound for use in the methods provided by the invention can be delivered using controlled or sustained-release delivery systems (e.g., capsules, biodegradable matrices). Exemplary delayed-release delivery systems for drug delivery that would be suitable for administration of the compositions of the disclosed compounds are described in U.S. Pat. No. 5,990,092 (issued to Walsh); U.S. Pat. No. 5,039,660 (issued to Leonard); U.S. Pat. No. 4,452,775 (issued to Kent); and U.S. Pat. No. 3,854,480 (issued to Zaffaroni), the entire teachings of which are incorporated herein by reference.

For preparing pharmaceutical compositions for use in the methods and kits provided by the invention, pharmaceutically acceptable carriers can either be solid or liquid. Solid form preparations include powders, tablets, pills, capsules, cachets, suppositories, and dispersible granules. For example, the compounds of the present invention may be in powder form for reconstitution at the time of delivery. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing agents, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical compositions for use in the methods and kits provided by the invention are preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form. The quantity of active ingredient in a unit dose preparation may be varied or adjusted to achieve the target plasma concentrations describe, above, e.g., from about 0.1 mg to about 1000.0 mg, e.g., from about 0.1 mg to about 100 mg or from about 1.0 mg to about 1000 mg. The dosages, however, may be varied depending upon the requirements of the patient, the severity of the condition being treated, the compound and the route of administration being employed. Determination of the proper dosage for a particular situation is within the skill in the art. Also, the pharmaceutical composition may contain, if desired, other compatible therapeutic agents.

In general, the methods for delivering the disclosed compounds and pharmaceutical compositions of the invention in vivo utilize art-recognized protocols for delivering the agent with the only substantial procedural modification being the substitution of the compounds represented by any one of the disclosed compounds for the drugs in the art-recognized protocols.

The compounds for use in the methods and kits provided by the invention may be administered by any route, preferably in the form of a pharmaceutical composition adapted to such a route, and would be dependent on the condition being treated. The compounds and compositions may, for example, be administered intravascularly, intramuscularly, subcutaneously, intraperitoneally, orally or topically. It will be obvious to those skilled in the art that the following dosage forms may comprise as the active ingredient, either compounds or a corresponding pharmaceutically acceptable salt of a compound of the present invention. A preferred method of administration for the compounds of the invention is oral administration.

In some embodiments, the composition may be administered parenterally via injection. Parenteral administration can include, for example, intraarticular, intramuscular, intravenous, intraventricular, intraarterial, intrathecal, subcutaneous, or intraperitoneal administration. Formulations for parenteral administration may be in the form of aqueous or non-aqueous isotonic sterile injection solutions or suspensions. These solutions or suspensions may be prepared from sterile powders or granules having one or more of the carriers mentioned for use in the formulations for oral administration. The compounds may be dissolved in polyethylene glycol, propylene glycol, ethanol, corn oil, benzyl alcohol, sodium chloride, and/or various buffers (e.g., sodium bicarbonate, sodium hydroxide).

For oral administration, the pharmaceutical compositions may be in the form of, for example, a tablet, capsule, suspension or liquid. The composition is preferably made in the form of a dosage unit containing a therapeutically effective amount of the active ingredient. Examples of such dosage units are tablets and capsules. For therapeutic purposes, the tablets and capsules can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example potato starch, flavoring or coloring agents, or acceptable wetting agents. Oral liquid preparations generally in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the compounds of the present invention, specifically anticipated in the case of scleroderma, may also be prepared in suitable forms to be applied to the skin, or mucus membranes of the nose and throat, and may take the form of creams, ointments, liquid sprays or inhalants, lozenges, or throat paints. Such topical formulations further can include chemical compounds such as dimethylsulfoxide (DMSO) to facilitate surface penetration of the active ingredient. Suitable carriers for topical administration include oil-in-water or water-in-oil emulsions using mineral oils, petrolatum and the like, as well as gels such as hydrogel. Alternative topical formulations include shampoo preparations, oral pastes and mouthwash.

For application to the eyes or ears, the compounds of the present invention may be presented in liquid or semi-liquid form formulated in hydrophobic or hydrophilic bases as ointments, creams, lotions, paints or powders.

For rectal administration the compounds of the present invention may be administered in the form of suppositories admixed with conventional carriers such as cocoa butter, wax or other glyceride. For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Delivery can also be by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract.

EXEMPLIFICATION

The literature describing cell lines derived from human tumors usually indicates that several forms of colonies may be distinguished a singly seeded cells grow to localized colonies of ~64 to thousands of cells. HT-29 and CAPAN-1 cell are not exceptions.

The metakaryotic and pre-metakaryotic cells of cell lines derived from human tumors are capable of unlimited division when plated as single cells on plastic or glass surfaces. However, most cells in such cell lines are eukaryotic cells capable of limited cell growth which growth cannot give rise to immortal colonies or populations of cells. This quality permits the line to be used in quantitative assays of cell killing important for distinguishing among agents and regimens that kill metakaryotic cells in preference to eukaryotic cells and vice versa.

Missing from the present discussion in the literature of both tumors and tumor derived lines is that of stem cells, metakaryotic and possibly pre-metakaryotic, increase their own number by symmetrical amitotic divisions and unknown modes of division, respectively. They are also responsible for the increase in tumor mass by the creation of first transition eukaryotic cells that by a series of binomial mitoses create a terminal cell population. When organized in adult tissue such as in the colonic crypts, the assemblage of maintenance stem cell and first through terminal cells create a turnover unit in which the apparently programmed cell deaths of terminal cells are matched by divisions of lower tier eukaryotic cells and the single maintenance stem cell at the crypt base. The turnover unit cell number remains approximately constant and the time interval between divisions of any cell is the same as the lifetime of any terminal cell. In the colon, for instance, Furth's data permitted calculation that this interval is ~128 days (Herrero-Jiminez et al., 1998, 2000).

As noted above, microtiter well studies of single cells of the exponentially growing HT-29 cell line indicated that this line closely imitates the growth of colonic crypts. Single cells betray different fates. A small fraction (~5-15% under present conditions) form colonies, button shaped or disperse, that express metakaryotic cell forms and grow to $>2^{13}$ cells and grow to millions of cells ($>2^{20}$) when trypsinized and transferred in a series of T-flasks. Applicants interpret these colonies and derived immortal populations to be the descendants of single metakaryotic or pre-metakaryotic stem cells.

However, most single cells give rise to colonies that range from 1 to ~2000 ($2^{11}$) cells that do not contain any visible metakaryotic cells and on trypsinized transfer do not increase in cell number. Applicants interpret these colonies that do not divide when placed as single, attached cells in microwells to be elements of turnover units containing ~$2^{11}$ terminal cells/unit. Applicants interpret the colonies of ~$2^{11}$ cells that do not grow on transfer to be derived from the second tier of the turnover unit which contains two cells. Colonies of limited size between 1 and $2^{11}$ cells are interpreted to be the products of growth of transition cell tiers three through eleven.

In this reproducible behavior the human tumor cell lines offered a means to test agents for metakaryocidal activity: metakaryocidal agents and regimens would reduce or eliminate the appearance of large colonies that could be propagated by serial trypsinized transfer. Metakaryocidal action could also be recognized by reduction of total colony number after trypsinized transfer of the HT-29 and like lines by the reduction in total colonies after treatment from that found in untreated control; flasks to about 90% of that number, the 10% difference representing the colonies that save for treatment would have arisen from a metakaryotic stem cell. An example of this kind of assay is illustrated in FIGS. 1, 2 and 3.

Multiple drugs have been tested based on their reported ability to interfere with wound healing (phleomycin) suppress cancer rates in the diabetic human population (metformin, sulphonyl ureas) or cure animal cancers in combination with known eukaryocidal drugs which alone are not effective (metformin, doxycycline). In particular drugs evaluated were reported to overcome "multidrug resistance" giving special priority to drugs that suppressed "multidrug resistance" (MDR). Cytotological and clonal assays have, so far, yielded equivalent results. Drug regimens that resulted in the appearance of pyknotic bell shaped nuclei also killed off cells capable of forming immortal colonies in HT-29 cell cultures. Cytologic results in HT-29 yielded identical results in the CAPAN-1 cell line.

Figure 1:
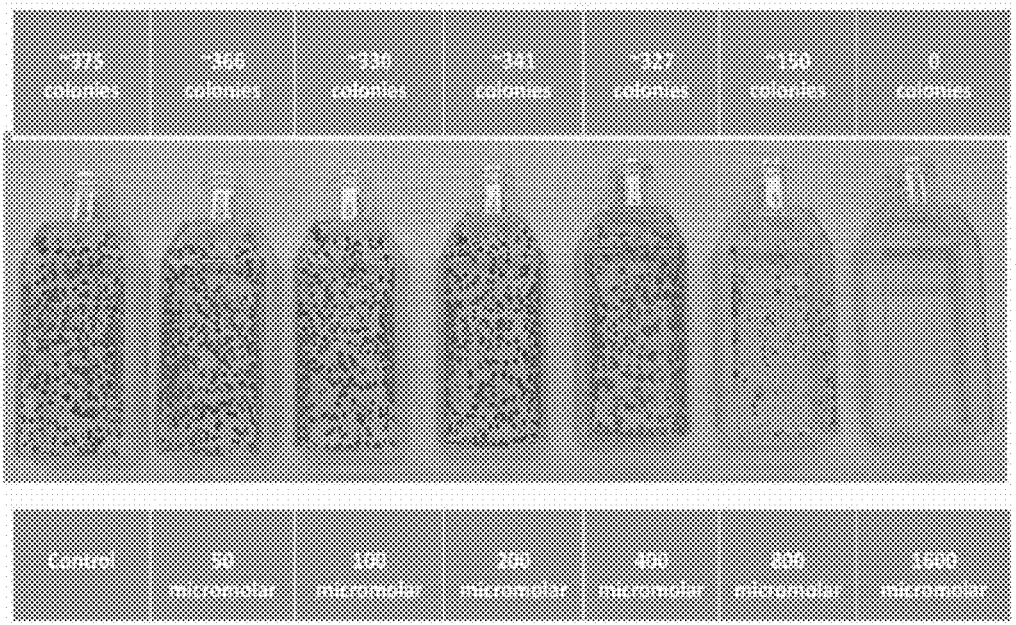
FIG. 1 is a photograph illustrating the result of treatment of HT-29 cells with zero and increasing levels of metformin for five weeks thus testing metformin as a metakaryocide in vitro.
Figure 3:
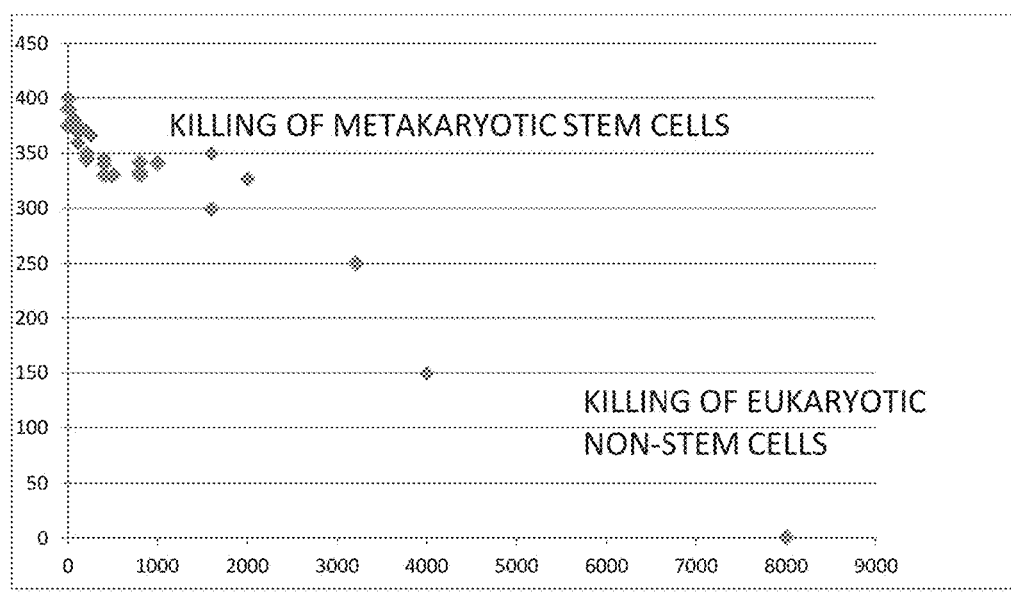
FIG. 3 is a scatterplot illustrating that the simple product of initial concentration×duration of exposure reveals a two phase survival curve with ~10-12% of colony forming stem cells killed by regimens of ~200-2000 μM-weeks.

Shown in FIGS. 1-3 are images of quantitative trials of different regimens (initial concentration, duration of exposure) of metformin in clonal assays using HT-29 cells. The image in FIG. 1 is that of a set of T-flasks with HT-29 cells surviving to form large colonies some five weeks after beginning of treatment with metformin under the conditions indicated. FIG. 1 is a photograph illustrating the experimental design for testing metformin as a metakaryocide in vitro. In the concentration range 100-400 micromolar an ~10% reduction in large colonies is observed that corresponds to immortal colonies in which metakaryotic cells are observed as stem cells. Large colonies surviving >100 micromolar are not immortal and do not contain metakaryotic stem cells.

FIG. 2 depicts a table of the recorded colony counts on each of the flasks of the first image. The image in FIG. 2 illustrates the reduction of large colonies forming five weeks after seeding HT-29 cells treated from day one for one, two or five weeks with the concentrations of metformin indicated. Total large colony numbers were reduced to a level about 10% less than in untreated control flasks at the concentration×duration of exposure treatments indicated with green colony counts. Applicants have discovered that ~10% reduction in large colonies observed as indicated corresponds to immortal colonies in which metakaryotic cells are observed as stem cells. Large colonies surviving treatment for >1600 micromolar for one week exposure or 800 micromolar for five weeks exposure are not immortal and do not contain metakaryotic stem cells. The cells in these surviving large colonies indicated by red type are wholly eukaryotic, grow to a terminal cell stage and do not further grow when transferred to new culture surfaces.

The graph in FIG. 3 is a scatter plot representation of the data of FIG. 2, showing the regimen dependent survival of what we interpreted to be metakaryotic stem cells in regimens that kill the metakaryotes plated. The Y-axis is the number of colonies on each test flask enumerated in FIG. 2 while the X-axis is the product of metformin concentration (micromolar) times the duration of the HT-29 cells to the drug (weeks). Typical of all metakaryocidal drugs discovered by applicants using HT-29 cells to date, the number of large colonies containing metakaryotic cells and capable of immortal growth in untreated flasks comprising some 10% of all large colonies observed (FIG. 1) decreases as a function of drug concentration×duration of exposure until no large colonies capable of immortal growth survive. For this drug this elimination of metakaryotic cell-containing immortal colonies is reached by ~200 micromolar-weeks while killing of mortal colonies is not observed until about 2000 micromolar weeks. Here it appears that a regimen holding patient plasma levels at or somewhat above 200 micromolar for an uninterrupted five week period would kill the cycling metakaryotic cells in a pathologic lesion in which metakaryotes comprise a stem cell lineage save for metakaryotic stem cells resistant to the drug metformin as are expected in tumors and metastases because of the high rate of mutation discovered in human organogenic stem cells (Sudo et al., 2008).

From the data of FIG. 3 a scatterplot illustrating that the log survival versus concentration×duration of metformin exposure may be constructed and used to calculate the treatment regimen for treating metakaryotic diseases. In this example the metformin-sensitive population (metakaryotic cells) has a survival fraction of $10^{-2}$ at ~200 μM weeks. From this, it is expected that a treatment of ~400 μM weeks could achieve a $10^{-4}$ survival, limited by hypothetical metformin-resistant mutants expected to arise at $>10^{-4}$ in metakaryotic disease lesions such as tumors or atherosclerotic plaques.

In tests of some sixteen drugs the choice of which was guided by inferences of applicants suggesting they might be metakaryocidal eight have demonstrated survival vs. concentration×duration function similar to that observed with metformin, e.g., doxicycline, verapamil and salinomycin, while one, reserpine, proved to have no detectable effect as a metakaryocide.

It should be understood that for all numerical bounds describing some parameter in this application, such as "about," "at least," "less than," and "more than," the description also necessarily encompasses any range bounded by the recited values. Accordingly, for example, the description at least 1, 2, 3, 4, or 5 also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that it is incorporated by reference in its entirety for all purposes as well as for the proposition that is recited. Where any conflict exits between a document incorporated by reference and the present application, this application will control. All information associated with reference gene sequences disclosed in this application, such as GeneIDs, Unigene IDs, or HomoloGene ID, or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., Pub Chem compound, Pub Chem substance, or Pub Chem Bioassay entries, including the annotations therein, such as structures and assays, et cetera) are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention including the working examples. For example, particular experimental parameters exemplified in the working examples can be adapted for use in the claimed invention piecemeal without departing from the invention. For example, for materials that are disclosed, while specific reference of each various individual and collective combinations and permutation of these compounds may not be explicitly disclosed, each is specifically contemplated and described herein. Thus, if a class of elements A, B, and C are disclosed as well as a class of elements D, E, and F and an example of a combination of elements, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus to the extent an element is described in one or more references known to the person having ordinary skill in the art, they may be excluded from the claimed invention by, inter alia, a negative proviso or disclaimer of the feature or combination of features.

LIST OF REFERENCES

Gostjeva, E. V., et al., "Bell-shaped nuclei dividing by symmetrical and asymmetrical nuclear fission have qualities of stem cells in human colonic embryogenesis and carcinogenesis," Cancer Genetics and Cytogenetics, 164: 16-24 (2006).

Gostjeva, E. V., et al., "Metakaryotic stem cell lineages in organogenesis of humans and other metazoans," Organogenesis, 5(4): 191-200 (2009).

Gostjeva, E. V., et al., "Nuclear Morphotypes in Human Embryogenesis and Carcinogenesis: Bell-Shaped Nuclei Show Stem-Like Properties In Vivo," Environmental and Molecular Mutagenesis, 47(6): 405 (2006).

Gostjeva, E. V., and Thilly, W. G., "Stem Cell Stages and the Origins of Colon Cancer: A Multidisciplinary Perspective," Stem Cell Reviews, 1: 243-252 (2005).

Gruhl, A. N., et al., "Human fetal/tumor metakaryotic stem cells: pangenomic homologous pairing and telomeric end-joining of chromatids," Cancer Genetics and Cytogenetics, 203(2): 203-208 (2010).

Herrero-Jimenez, P., et al., "Mutation, cell kinetics, and subpopulations at risk for colon cancer in the United States," Mutat. Res., 400: 553-578 (1998).

Herrero-Jimenez, P., et al., "Population risk and physiological rate parameters for colon cancer. The union of an explicit model for carcinogenesis with the public health records of the United States," Mutat. Res., 447: 73-116 (2000).

Kini, L. G. et al., "Mutator/hypermutable fetal/juvenile metakaryotic stem cells and human colorectal carcinogenesis," Frontiers ONCOLOGY, 3(267): 1-17 (2013).

Leong, P. M. et al., "Variance estimation in single-cell mutation assays: comparison to experimental observations in human lymphoblasts at 4 gene loci," Mutation Research, 150: 403-410 (1985).

Sudo, H. et al., "Distributions of five common point mutants in the human tracheal-bronchial epithelium," Mutation Research, 596:113-127 (2006).

Sudo, H. et al., "Fetal juvenile origins of point mutations in the adult human tracheal-bronchial epithelium: Absence of detectable effects of age, gender or smoking status," Mutation Research 646:25-40 (2008).

Thilly, W. G., et al., "Metakaryotic stem cell nuclei use pangenomic dsRNA/DNA intermediates in genome replication and segregation," Organogenesis, 10(1): 1-9 (2014).

Thilly W. G, and Heidelberger, C. Cytotoxicity and mutagenicity of ulltraviolet irradiation as a function of the interval between split doses. Mutation Research 17 287-290 (1973).

U.S. Pat. No. 7,427,502 issued Sep. 23, 2008, Gostjeva et al.
U.S. Pat. No. 7,977,092 issued Jul. 12, 2011, Gostjeva et al.
U.S. Pat. No. 8,465,943 issued Jun. 18, 2013, Gostjeva et al.
U.S. Pat. No. 8,940,500 issued Jan. 27, 2015, Gostjeva et al.
U.S. Published Application No. US 2013/0203048 A1 published Aug. 8, 2013, Thilly et al.
U.S. Published Application No. US 2014/0369934 A1 published Dec. 18, 2014, Thilly et al.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a human patient with cancer, wherein the cancer results from excessive metakaryotic stem cell growth, the method comprising administering to the patient a therapeutically effective amount of doxycycline, wherein the administration of doxycycline to the patient is continuous administration for a time sufficient to achieve and maintain a therapeutically effective amount of doxycycline in the patient's plasma to kill the metakaryotic stem cells, thereby treating the cancer.

2. The method of claim 1 wherein the cancer is pancreatic cancer.

3. The method of claim 2, wherein the effective amount of doxycycline achieves and maintains a plasma concentration of about 2 µM to about 50 µM.

4. The method of claim 2 wherein the metakaryocidal agent is administered for a duration of about 2 to about 52 weeks.

5. The method of claim 1, further comprising the administration of one, or more, additional metakaryocidal agents to the subject.

6. The method of claim 5, wherein the one, or more metakaryocidal agents are administered sequentially.

7. The method of claim 5, wherein the one, or more metakaryocidal agents are administered in a combination of agents, wherein the combination comprises from one to five or more agents.

8. The method of claim 5 wherein the metakaryocidal agent is administered for duration of about 2 to about 52 weeks.

9. The method of claim 5, wherein the treatment of the disorder further includes treatment with x-rays or a eukaryocidal chemotherapy treatment.

10. The method of claim 1, wherein the treatment of the disorder further includes treatment with x-rays or a eukaryocidal chemotherapy treatment.

* * * * *